United States Patent [19]

Charmot et al.

[11] Patent Number: 4,737,533
[45] Date of Patent: Apr. 12, 1988

[54] DRY MATERIAL WHICH CAN BE HYDRATED INTO AN AQUEOUS GEL, CONTAINING DISPERSED POLYMER PARTICLES, PROCESS FOR THE PREPARATION THEREOF AND USE THEREOF IN BIOLOGICAL APPLICATIONS

[75] Inventors: Dominique Charmot, Paris; Jean-Claude Daniel, Fontenay/Sous/Bois, both of France

[73] Assignee: Rhone-Poulenc Chimie, Courbevoie, France

[21] Appl. No.: 37,151

[22] Filed: Apr. 10, 1987

[30] Foreign Application Priority Data

Apr. 15, 1986 [FR] France ................ 86 05347

[51] Int. Cl.$^4$ ............... C08L 89/00; C08L 33/26; C08L 25/04; B01D 15/00
[52] U.S. Cl. ................. 524/22; 264/331.11; 264/331.12; 264/331.13; 524/24; 524/56; 524/58; 524/386; 524/431; 524/503; 524/916; 525/902
[58] Field of Search ............ 525/902; 524/916, 22, 524/56, 58, 24, 386, 431; 264/331.11, 331.13, 331.12

[56] References Cited

U.S. PATENT DOCUMENTS

| 4,048,377 | 9/1977 | Boschetti et al. |
| 4,294,921 | 10/1981 | Yamaguchi et al. ............... 524/22 |
| 4,320,040 | 3/1982 | Fujita et al. ........................ 524/916 |
| 4,448,639 | 5/1984 | Long ................................... 428/703 |
| 4,500,670 | 2/1985 | McKinley et al. ................ 524/916 |
| 4,521,567 | 6/1985 | Arndt et al. ....................... 525/902 |
| 4,525,509 | 6/1985 | Hunter et al. ..................... 524/916 |
| 4,548,734 | 10/1985 | Chaux et al. |
| 4,548,869 | 10/1985 | Ogawa et al. ..................... 524/521 |
| 4,548,870 | 10/1985 | Ogawa et al. ..................... 524/521 |
| 4,666,975 | 5/1987 | Yamasaki et al. ................. 524/733 |
| 4,668,715 | 5/1987 | Phillips ............................. 524/916 |

FOREIGN PATENT DOCUMENTS 87786 9/1983 European Pat. Off. .
1577956 10/1980 United Kingdom .

*Primary Examiner*—Herbert J. Lilling
*Attorney, Agent, or Firm*—Finnegan, Henderson, Farabow, Garrett & Dunner

[57] ABSTRACT

Dry material which can be hydrated into an aqueous gel comprising (1) a matrix comprising a macromolecular substance A, capable of forming a porous aqueous gel when it is in the presence of water, (2) a water-soluble linear polymer B, (3) a plasticizer for the macromolecular substance A and, (4) dispersed in the matrix, particles of a polymer C obtained from at least one water-immiscible monomer.

The material can be obtained by mixing an aqueous solution of A with the polymer B, the plasticizer and a latex of polymer C, followed by cooling, shaping and drying of the aqueous gel obtained.

The dry material can be used in biological applications after rehydration.

32 Claims, No Drawings

DRY MATERIAL WHICH CAN BE HYDRATED INTO AN AQUEOUS GEL, CONTAINING DISPERSED POLYMER PARTICLES, PROCESS FOR THE PREPARATION THEREOF AND USE THEREOF IN BIOLOGICAL APPLICATIONS

The present invention relates to a dry material which can be hydrated into an aqueous gel containing dispersed polymer particles, to a process for the preparation thereof and to the use thereof in biological applications, such as diagnostic tests, cell culture, affinity chromatography and carriers for drugs.

European patent application No. 87,786 describes beads comprising a hydrated agarose gel matrix containing microspheres or a powder of a polyaldehyde, for example, polyacrolein. These beads may be used in various applications such as affinity chromatography, blood perfusion, ion exchange resins and diagnostic tests.

The disadvantages of such products lie in the problems encountered while implementing them, i.e., the difficulty of synthesizing the polyacroleins and the toxicity of the acrolein monomer. Additionally, these beads are in the form of a moist gel which is difficult to handle.

French patent publication No. 2,297,879 discloses a process for the preparation of dried plates containing agarose or gelose which can be rehydrated and used in techniques such as immunodiffusion and electrophoresis. The process consists of forming, on a support, an aqueous gel film of agarose or gelose containing a water-soluble acrylamide polymer and then drying the gel film. These plates are advantageously capable of being stored for a prolonged period of time and rehydrated at the desired time. However, the plates can only be used within a restricted field of application.

The binding of proteins to polymer particles in an aqueous dispersion is also known, for example, by absorption, when polystyrene particles are used, or by covalent bonding when polymers having reactive groups are employed. The advantage offered by latices resides in the large specific surface area developed by the particles and in their wide range of available chemical groups. On the other hand, their disadvantage lies in their colloidal instability, particularly towards electrolytes, and in the difficulty of recovering the particles to which the substances to be isolated are bound.

The present invention relates to a dry material comprising a matrix capable of forming a porous gel in the presence of water. The matrix contains dispersed particles of a polymer derived from a water-immiscible monomer. This product has the advantage of being easy to handle and of lending itself to various applications.

The dry material which can be hydrated into an aqueous gel which forms the subject of the invention comprises;
(a) a matrix comprising a macromolecular substance A capable of forming a porous aqueous gel when it is in the presence of water,
(b) a water-soluble linear polymer B,
(c) a plasticizer for the macromolecular substance A, and
(d) dispersed in the matrix, particles of a polymer C obtained from at least one water-immiscible monomer, wherein the polymer C, which can also contain reactive functional groups, has a glass transition temperature greater than 30° C, preferably greater than 60° C., and wherein all the components (a)-(d) are present in amounts effective to obtain the dry material.

Amounts of components (a)-(d) effective to obtain the dry material which can be hydrated into an aqueous gel can be readily selected by those skilled in the art without undue experimentation. Preferred amounts of each component are described below.

The hydratable dry material which forms the subject of the invention may be utilized in any form, such as films, plates, sticks, pellets and beads.

The macromolecular substance A forming the matrix may be chosen from amongst polysaccharides, proteins, and the like. The aqueous solutions of the macromolecular substance A are capable of forming a gel after preferably cooling to a temperature of from about 30 to about 80° C. Suitable macromolecular substances A include polygalactoses, such as agarose or gelose, and pectins and proteins such as gelatin and collagen.

The water-soluble linear polymer B present in the product of the invention may be chosen from amongst water-soluble polymers. The viscosity of these polymers at 22° C. in a 5% by weight aqueous solution is preferably less than 17,000 centipoises, and more preferably, less than 6,000 centipoises.

Examples of polymer B include polyethylene glycols having a weight average molecular mass of about at least 1,000, polyvinyl alcohol, poly(vinylpyrrolidone), hydroxyalkyl celluloses, carboxyalkyl celluloses and, very particularly, linear polyacrylamides.

The term "polyacrylamides" refers to linear homopolymers of acrylamide as well as to linear copolymers of acrylamide and at least one other comonomer of the vinylpyrrolidone type, or acrylic or methacrylic esters of the ethylene glycol monomethacrylate or ethylene glycol monoacrylate type.

The preferred quantity of water-soluble linear polymer B present in the hydratable dry material is approximately 2 to 10 times the weight of the dry matrix.

Examples of plasticizers of the macromolecular substance A include polyhydric alcohols such as glycols, glycerol, sorbitol and polyethylene glycols with weight average molecular masses less than 400.

The preferred quantity of plasticizer is approximately 1 to 3 times the weight of the dry matrix.

The particles based on polymer C dispersed in the matrix preferably have a particle size of the order of 0.05 to 20 $\mu$m, more preferably 0.1 to 3 $\mu$m.

The preferred weight of the particles employed is approximately 0.1 to 20 times, more preferably, approximately 1 to 10 times, the weight of the dry matrix.

The polymer C is obtained from at least one unsaturated water-immiscible monomer. The term "water-immiscible monomer" refers to monomers which have a water solubility of less than 5% by weight. Representative water-immiscible monomers include:
vinylaromatic monomers such as styrene and vinyltoluene;
alkyl esters of $\alpha$-$\beta$ unsaturated acids, such as methyl and ethyl acrylates and methacrylates;
esters of unsaturated carboxylic acids, such as vinyl acetate;
vinyl chloride, vinylidene chloride;
dienes including conjugated dienes, such as butadiene;

water-immiscible monomers, including unsaturated monomers, containing at least one nitrile group, such as acrylonitrile, and siloxanes.

In a first variant, polymer C may be a copolymer obtained from at least one water-immiscible monomer and a small quantity, not exceeding 10% by weight relative to the total weight of the water-immiscible monomer(s), preferably not exceeding 4% by weight, of at least one comonomer carrying ionogenic or reactive groups such as $-SO_3H$, $-OSO_3H$, $-N^+R_3$, $-COOH$, $-OH$, $-NH_2$, $-NR_2$, $$-CH-CH_2,\atop\diagdown O \diagup$$

$-\phi CH_2Cl$, $-CONH_2$ and the like, wherein R represents a $C_1-C_4$, preferably $C_1-C_2$, alkyl radical.

Examples of such comonomers include:
vinylbenzene sulfonate, preferably divinylbenzene sulfonate, sulfoalkyl esters of unsaturated acids, such as 2-sulfoethyl methacrylate;
unsaturated carboxylic acids, such as acrylic acid, methacrylic acid, maleic acid, and itaconic acid;
hydroxyalkyl acrylates or methacrylates, such as hydroxyethyl acrylate and hydroxypropyl acrylate;
aminoalkyl esters of unsaturated acids, such as 2-aminoethyl methacrylate;
acrylamide;
vinylbenzyl chloride and
glycidyl methacrylate.

In a second variant, polymer C may be an alkali-soluble or acid-soluble copolymer, i.e., capable of being solubilized in the form of an aqueous copolymer solution when the pH is either alkaline or acidic.

These copolymers are obtained from at least one water-immiscible monomer and 4 to 90%, preferably 10 to 50% by weight relative to the total weight of the water-immiscible monomer(s) of at least one anion-producing comonomer in the case of alkali-soluble copolymers or at least one cation-producing comonomer in the case of acid-soluble copolymers. The proportion of comonomer depends, of course, on the hydrophilicity of the latter.

Examples of anion-producing comonomers include unsaturated carboxylic acids such as itaconic acid, maleic acid and fumaric acid.

The solubilization pH of the alkali-soluble copolymers thus formed is generally of the order of from about 6 to about 11. Examples of cation-producing comonomers include those of the following formulae (1) and (2):

(1) N-ω-dialkylaminoalkyl)amides of unsaturated carboxylic acids of the formula:

$$CH_2=\underset{R_1}{\underset{|}{C}}-\underset{}{\overset{O}{\overset{\|}{C}}}-NH-R_2-N\diagup^{R_3}_{\diagdown R'_3}$$

in which
$R_1$ represents a hydrogen atom or a $C_1-C_4$, preferably a $C_1-C_2$, alkyl group,
$R_2$ represents a $C_1-C_{12}$, preferably a $C_1-C_8$, alkylene group, and
$R_3$ and $R'_3$, which may be identical or different, represent a $C_1-C_6$, preferably $C_1-C_4$, alkyl group or phenyl group, substituted, if required, with a $C_1-C_9$ alkyl radical.

Exemplary compounds which correspond to the formula (1) include dimethylaminomethyl acrylamide or methacrylamide and dimethylaminoethyl acrylamide or methacrylamide.

(2) Unsaturated amino esters of the formula:

$$CH_2=\underset{R'_1}{\underset{|}{C}}-\underset{}{\overset{O}{\overset{\|}{C}}}-O-R'_2-N\diagup^{R''_3}_{\diagdown R'''_3}$$

in which
$R'_1$ represents a $C_1-C_5$, preferably a $C_1-C_2$, alkyl group,
$R'_2$ represents a straight-chain or branched alkylene group containing at least 2 carbon atoms, preferably a $C_2-C_{12}$ group, and more preferably a $C_2-C_8$ group, and $R''_3$ and $R'''_3$, which may be identical or different, represent a $C_1-C_6$, preferably a $C_1-C_4$, alkyl group substituted, if required, with a hydroxy radical or a phenyl group which is substituted, if required, with a $C_1-C_9$ alkyl radical,
wherein the total number of carbon atoms contained in the $R'_2$, $R''_3$ and $R'''_3$ radicals is greater than 8, preferably greater than or equal to 10.

Di-tert-butylaminoethyl methacrylate, di-tert-butylaminopropyl methacrylate and dipentylaminoethyl methacrylate are exemplary compounds which correspond to the formula (2).

The solubilization pH of the acid-soluble copolymers thus formed is generally less than 8 and preferably less than 5.

In a particular case, polymer C can be an alkali-soluble copolymer having a weight average molecular mass of less than 100,000, preferably less than 50,000.

In a third variant, polymer C may be "sensitized," which means that biologically active substances such as antibodies, antigens, drugs and enzymes are immobilized on the particles of polymer C (the term "polymer C," corresponds to the definition given above and includes the two copolymer variants described above and very particularly includes the alkali-soluble and acid-soluble polymers). In particular, the alkali-soluble or acid-soluble polymer C can have a weight average molecular mass less than 100,000 and can also be sensitized by a biologically active substance.

In another variant, the particles of polymer C included in the matrix are polymer particles which can be magnetized.

The particles which can be magnetized can contain from 0.5 to 50% by weight, preferably from 0.5 to 35%, and more preferably from 0.7 to 20%, of a magnetic charge the size of which can be less than 1 μm and preferably is from 0.002 to 0.05 μm. The magnetic charge is obviously sufficiently fine to be capable of being included in the polymer particles.

This magnetic charge may consist, for example, of:
metals or their alloys such as iron, iron-silicon, nickel, cobalt, or their alloys with molybdenum, chromium, copper, vanadium, manganese, aluminum or titanium;
iron oxides such as $Fe_3O_4$ or $\gamma-Fe_2O_3$ alone or in combination or in mixture with other oxides such as oxides of cobalt, manganese, zinc, barium and rare earths; and chromium dioxide.

The dry material which can be hydrated and which forms the subject of the invention, may be obtained by carrying out the following steps:

(1) mixing, in amounts effective to form, after the cooling (2) and drying (3) steps described below, the dry material,
   (a) an aqueous solution of a macromolecular substance A capable of forming, after preferably cooling to a temperature of 30 to 80° C., a porous aqueous gel when the substance A is in the presence of water, at a preferred concentration of the substance A effective for forming the gel at a temperature of 30° to 80° C.,
   (b) a water-soluble linear polymer B,
   (c) a plasticizer for the macromolecular substance A, and
   (d) a latex of a polymer C derived from at least one water-immiscible monomer, wherein the polymer C has a glass transition temperature greater than 30° C., preferably greater than 60° C., and wherein the polymer C can also contain reactive functional groups, if required, and wherein mixing occurs at a temperature greater than the gelling temperature of the aqueous solution of the macromolecular substance A;

(2) cooling the resultant mixture to a temperature less than the gelling temperature of the aqueous solution of the macromolecular substance A and shaping the aqueous gel obtained during the cooling; and (3) drying the shaped aqueous gel at a temperature less than the gelling temperature of the aqueous solution of the molecular substance A to obtain the dry material.

The raw materials employed for carrying out the mixing step are those already described above. As described above, effective amounts of each component (a)–(d) can be readily selected by one skilled in the art without undue experimentation. Preferred amounts of components (a)–(d) are given below.

The mixing step 1) is carried out at a temperature greater than that for the formation of an aqueous gel of the macromolecular substance A. The concentration of the macromolecular substance in the aqueous solution corresponds to the concentration required for the formation of such a gel. Thus, for example, when the macromolecular substance is agarose, the mixing step is carried out using a 0.5 to 2% by weight aqueous solution of agarose, at a temperature greater than 40° C. and generally less than or equal to 90° C.

The preferred quantity of water-soluble linear polymer B employed is approximately 2 to 10 times the weight of the dry macromolecular substance A.

The preferred quantity of plasticizer employed is approximately 1 to 3 times the weight of the dry macromolecular substance A.

The water-soluble linear polymer B and the plasticizer may be employed in a form either completely dissolved in the aqueous solution of the macromolecular substance A or dissolved in part in the aqueous solution and in part in the latex of the polymer C.

The latex employed preferably contains from 5 to 30%, more preferably from 10 to 15%, by weight of polymer particles.

The quantity of latex employed is preferably equivalent to a quantity of polymer C which is 0.1 to 20 times, more preferably approximately 1 to 10 times, the weight of the dry macromolecular substance A.

When, according to the third variant of the structure of the product which forms the subject of the invention, the particles of polymer C carry immobilized biologically active substances, the active substances may be introduced into the medium, either directly by using a latex of particles of polymer C to which the substances have been bound by physical absorption or chemically by covalency, or indirectly, after the encapsulation of the particles of polymer C by the aqueous gel of the macromolecular substance A, by the migration of the active substances through the gel of the macromolecular substance A followed by immobilization by physical absorption or by covalency.

The covalent binding of biologically active molecules to polymer particles may be carried out by a coupling reaction, which involves the surface groups of the polymer particles and the functional groups of the biologically active molecule to be bound.

This coupling reaction can be carried out according to methods which are well known, for example:
   using coupling agents (such as glutaraldehyde and water-soluble carbodiimide), and
   by activating the functional groups of the polymer (for example by diazotization, by the action of, for example, cyanogen bromide or hydrazine) and then reaction with the molecule to be bound.

When a dry material which can be hydrated and magnetized is desired, the latex of the polymer employed contains polymer particles which can be magnetized.

The latices may be obtained according to known processes, for example, according to processes described in European patent No. 38,730 or in U.S. Pat. No. 4,157,323, the disclosures of which are specifically incorporated by reference herein.

The operation of shaping the aqueous gel obtained by cooling is carried out according to well-known methods which depend on the shape desired for the final dry material.

When the macromolecular substance employed is agarose, the cooling stage (2) can be favorably carried out at a temperature of 15° to 25° C.

Once shaped, the aqueous gel is dried in a stream of air, at a temperature close to that of the cooling stage.

A gel in the form of a film may be obtained by pouring the mixture obtained in the mixing stage described above on a glass plate, and allowing it to cool to convert the liquid film deposited into an aqueous gel film. The aqueous gel film may then be demolded and dried as mentioned above.

A particularly interesting procedure for shaping the aqueous gel and drying is that described in the French patent publication No. 2,297,879, the disclosure of which is specifically incorporated by reference herein.

The shaping process consists of pouring the mixture obtained in the mixing stage described above onto a support consisting of a transparent thermoplastic plate GEL-BOND, marketed by LKB, which is placed on a horizontal glass plate, allowing the mixture to cool to form an aqueous gel which adheres to the plate, and covering the aqueous gel film with a regenerated cellulose-based sheet ("Cellophane" marketed by Rhone-Poulenc) soaked in an aqueous solution of glycerol. The sheet of regenerated cellulose is folded back under the glass plate.

The whole is then dried at an ambient temperature under a stream of air. The glass plate is finally detached from the plastic plate coated with the dry material which can be hydrated.

The dry material which can be hydrated into an aqueous gel containing dispersed polymer particles and which forms the subject of the invention has the advantage of combining the positive properties of the matrix, i.e., of being (1) capable of being hydrated at the desired time into a porous aqueous gel in such forms as films, plates, sticks, pellets and beads which can be easily handled, (2) compatible even with aqueous media with high concentrations of electrolytes, and (3) permeable to high molecular weight proteins, with the positive properties of the polymer particles derived from a water-immiscible monomer, viz. having a high and controlled specific surface area and a wide range of available chemical groups on the surface.

The product is particularly valuable for its uses in biological applications. The porous nature of the gel of the macromolecular substance A enables proteins to reach the particles of polymer C and to become bound thereto by absorption or covalency.

Many biologically active substances such as antibodies, antigens, drugs, and enzymes may thus be immobilized. Depending on the nature of the immobilized biologically active substance, it is possible to obtain a support capable of being advantageously used in immuno-enzymatic or radio-immunological tests, in affinity chromatography, in extracorporeal purification systems, as an enzymatic catalyst in biotechnology, as a device for the control of drug administration (drug release system) and as a cell culture medium.

The products of the invention containing particles of polymer C which are alkali-soluble or acid-soluble, which have a low molecular mass, such as less than 100,000, and on which biologically active substances are immobilized, are particularly useful in affinity chromatography. For example, if such a product containing alkali-soluble polymer particles on which antibodies have been immobilized is brought into contact with a mixture of antigens, the antigen recognized by the antibody becomes bound to the particle and remains bound thereto after eluting the mixture of antigens. A simple increase in pH enables the polymer particles to dissolve and to migrate through the porous gel releasing the antigen-antibody complex formed.

The alkali-solubility (or acid-solubility) property of the polymer C of any molecular mass may be taken advantage of to form carriers for drugs in which the active principle is released by a simple change in pH.

Another advantage of the dry material which can be hydrated into an aqueous gel containing dispersed polymer particles and which forms the subject of the invention consists of a judicious choice of the nature of the macromolecular substance A to give the possibility of selectively recovering the particles of polymer C, to which the substances to be isolated are bound, by destroying, after use, the macromolecular substance A. Such destruction can be accomplished, for example, by enzymatic degradation when the macromolecular substance A is collagen.

The following examples are given by way of illustration and cannot be considered as limiting the scope or the spirit of the claimed invention.

EXAMPLE 1

Preparation of a dry plate which can be rehydrated, containing 0.8 micron-diameter polystyrene particles.

8 g of linear polyacrylamide, the viscosity of which in a 5% aqueous solution at 22° C. is in the vicinity of 6,000 centipoises are dissolved, at ambient temperature, in 52 g of water containing 2 g of glycerol, for a period of approximately 48 hours.

48 g of the latex ESTAPOR ®K 080 (latex marketed by Rhone-Poulenc and consisting of monodispersed 0.8 micron polystyrene particles) with a dry matter content of 41% are then added to this preparation.

In a separate operation, 2 g of agarose are dissolved in 100 ml of demineralized water containing 2 g of glycerol, in a boiling water-bath.

The two solutions are brought to 50° C. and then mixed, stirring slowly, to avoid the formation of air bubbles.

The mixture obtained is poured onto a transparent plastic support GEL-BOND (marketed by LKB) placed on a horizontal glass plate, so as to obtain a 0.8 mm-thick layer of gel.

The whole is cooled to ambient temperature; the aqueous gel adheres to the support.

The aqueous gel film is then covered with a sheet of "Cellophane" (marketed by Rhone-Poulenc) which was previously soaked in a glycerol/water solution containing 2% glycerol. The edges of the "Cellophane" sheet are folded back under the glass plate and the assembly is dried at ambient temperature under a current of air for 15 hours.

The assembly consisting of the dried gel film which is white in appearance, the GEL-BOND support and the "Cellophane" sheet is then detached from the glass plate and stored at ambient temperature.

The rehydration of the dried gel film can be carried out by immersing the dried gel film, which is freed from the GEL-BOND support and the "Cellophane" sheet, in water at ambient temperature. This water is renewed to remove the linear polyacrylamide, and the rehydration is accompanied by a significant swelling of the gel without the release of the polystyrene particles.

The specific surface area of the dry material calculated per gram of dry matter is 4.4 m$^2$.

EXAMPLE 2

Preparation of a dry plate which can be rehydrated, containing 0.3 micron-diameter carboxylated polystyrene particles.

The operations described in example 1 are carried out using the following raw materials:

| | |
|---|---|
| agarose | 3 g |
| glycerol | 6 g (3 g + 3 g) |
| polyacrylamide | 6 g |
| ESTAPOR ® K1-030 latex | 40 g |

(the ESTAPOR K1-030 latex, marketed by Rhone-Poulenc, is an aqueous dispersion of size-graded particles of carboxylated polystyrene; the measured diameter of the particles is 0.326±0.010 micron; the concentration of surface-COOH groups is 273 microequivalents per gram of dry particles; the dry matter content is 30%).

A dry gel which can be rehydrated is thereby obtained.

The specific surface area of the dry material calculated per gram of dry matter is 13.2 m².

The concentration of available carboxyl groups per gram of dry matrix is 192 microequivalents.

EXAMPLE 3

Preparation of a dry plate which can be rehydrated, containing 0.2 micron-diameter chlorobenzylated polystyrene particles.

The operations described in example 1 are carried out using the following raw materials:

| | |
|---|---|
| agarose | 1 g |
| glycerol | 2 g (1 g + 1 g) |
| polyvinyl alcohol (RHODOVIOL 4-125 marketed by Rhone-Poulenc) | 5 g |
| ESTAPOR K10-020 latex | 50 g |

(ESTAPOR K10-020 latex, marketed by Rhone-Poulenc, is an aqueous dispersion of size-graded particles of chlorobenzylated polystyrene; the measured diameter of the particles is 0.210±0.006 micron; the concentration of —$\phi$—$CH_2Cl$ groups is 200 microequivalents per gram of dry particles; the dry matter content is 10%).

A dry gel which can be rehydrated is thereby obtained.

The specific surface area of the dry material calculated per gram of dry matter is 11 m².

The concentration of available —$\phi$—$CH_2Cl$ groups per gram of dry matrix is 77 microequivalents.

The presentation of the gel in its dry form enables the chlorobenzyl groups to be retained intact and their hydrolysis to be avoided. This represents a significant advantage as it has been observed that chlorobenzylated polystyrene latices present problems during storage; in fact, during storage, the pH of such latices, which is initially 7-8, may go down as far as 2, with the release of chloride ions and the formation of benzyl alcohol groups by the partial hydrolysis of the chlorobenzylated groups present on the surface.

EXAMPLE 4

Preparation of a dry support which can be rehydrated, containing magnetic carboxylated polystyrene particles.

The operation described in example 1 is carried out using the following raw materials:

| | |
|---|---|
| agarose | 2 g |
| sorbitol | 5 g (2.5 g + 2.5 g) |
| polyvinylpyrrolidone (LUVISKOL K15 marketed by B.A.S.F.) | 4 g |
| ESTAPOR MS1-070/25 latex | 150 g |

(the ESTAPOR MS1-070/25 latex, marketed by Rhone-Poulenc, is an aqueous dispersion of carboxylated polystyrene-based magnetic particles containing 25% by weight of magnetite $Fe_3O_4$; the mean diameter is 0.7 micron; the concentration of carboxyl groups is 65 microequivalents per gram of dry particles; the dry matter content is 10%).

The dry plate obtained is cut into 1 mm-sided squares.

It is observed that after rehydration, the pieces can be magnetized using a laboratory magnet.

EXAMPLE 5

Preparation of a dry plate which can be rehydrated, containing polymer particles which are alkali-soluble in nature.

The operations described in example 1 are carried out using the following raw materials:

| | |
|---|---|
| agarose | 4 g |
| ethylene glycol | 4 g (2 g + 2 g) |
| polyacrylamide | 8 g |
| alkali-soluble latex | 20 g |

(the alkali-soluble latex is an aqueous dispersion of particles of a styrene/methacrylic acid/ethyl acrylate terpolymer in a weight ratio of 18:41:11; the particle size is of the order of 0.15 micron; the dry matter content is 38.5%; this terpolymer dissolves in water as soon as the pH is greater than 8; its viscosity in a 10% aqueous solution is less than 150 centipoises at pH 9).

The dry plate obtained is rehydrated by immersing in slightly alkaline water (pH 9); it becomes translucent while maintaining its cohesiveness and releases the polymer forming the particles into the water.

EXAMPLE 6

Preparation of a dry plate which can be rehydrated, containing polymer particles, which are acid-soluble in nature The operations described in example 1 are carried out using the following raw materials:

| | |
|---|---|
| agarose | 4 g |
| ethylene glycol | 4 g (2 g + 2 g) |
| polyacrylamide | 8 g |
| alkali-soluble latex | 20 g |

(the acid-soluble latex is an aqueous dispersion of particles of a vinylacetate/diethylaminoethyl acrylate copolymer with a weight ratio of 90:10; the particle size is of the order of 0.15 micron; the dry matter content is 38%; this copolymer dissolves in water as soon as the pH is less than 3; its viscosity in a 10% aqueous solution is less than 150 centipoises at pH 2).

The dry plate obtained is rehydrated by immersing in neutral water; the rehydrated plate becomes translucent while maintaining its cohesiveness and releases the polymer forming the particles into the water if the pH is lowered below 2 with dilute hydrochloric acid.

We claim:

1. A dry material which can be hydrated into an aqueous gel, comprising:
    (a) a matrix comprising a macromolecular substance A capable of forming a porous aqueous gel when it is in the presence of water;
    (b) a water-soluble linear polymer B;
    (c) a plasticizer for the said macromolecular substance A; and
    (d) dispersed in said matrix, particles of a polymer C obtained from at least one water-immiscible monomer, wherein the polymer C has a glass transition temperature greater than 30° C. and can also contain reactive functional groups, and wherein all the components (a)–(d) are present in an amount effective to achieve said dry material.

2. The dry material of claim 1, wherein said macromolecular substance A is capable of forming, after cooling to a temperature of 30° to 80° C., a porous aqueous gel when it is in the presence of water and wherein said water-soluble linear polymer B has a viscosity at 22° C. in a 5% by weight aqueous solution of less than 17,000 centipoises.

3. The dry material of claim 2, wherein said water-soluble linear polymer B has a viscosity at 22° C. in a 5% by weight aqueous solution of less than 6,000 centipoises.

4. The dry material of claim 1, wherein the macromolecular substance A is agarose.

5. The dry material of claim 4, wherein the water-soluble linear polymer B is a linear polyacrylamide.

6. The dry material of claim 1, wherein the water-soluble linear polymer B is a linear polyacrylamide.

7. The dry material of claim 1, wherein the quantity of water-soluble linear polymer B present in the dry material which can be hydrated is approximately 2 to 10 times the weight of the dry matrix.

8. The dry material of claim 1, wherein the plasticizer for the macromolecular substance A is a polyhydric alcohol.

9. The dry material of claim 1, wherein the quantity of plasticizer is approximately 1 to 3 times the weight of the dry matrix.

10. The dry material of claim 1, wherein the polymer C has a glass transition temperature greater than 60° C.

11. The dry material of claim 1, wherein the polymer C is derived from at least one water-immiscible monomer selected from the group consisting of a vinylaromatic monomer, an alkyl ester of an α-β unsaturated acid, an ester of an unsaturated carboxylic acid, vinylchloride, vinylidene chloride, a conjugated diene, an unsaturated monomer containing at least one nitrile group, and a siloxane.

12. The dry material of claim 1, wherein the polymer C is obtained from (1) at least one water-immiscible monomer and (2) less than 10% by weight, relative to the total weight of the water-immiscible monomer(s), of at least one comonomer which carries an ionogenic or reactive group.

13. The dry material of claim 12, wherein said comonomer is selected from the group consisting of vinylbenzene sulfonate, a sulfoalkyl ester of an unsaturated acid, an unsaturated carboxylic acid, a hydroxyalkyl acrylate or methacrylate, an aminoalkyl ester of an unsaturated acid, acrylamide, vinylbenzene chloride and glycidyl methacrylate.

14. The dry material of claim 1, wherein the polymer C is an alkali-soluble or acid-soluble polymer.

15. The dry material of claim 1, wherein the particles of polymer C can be magnetized.

16. The dry material of claim 1, wherein the particles of polymer C have a particle size of the order of 0.05 to 20 μm.

17. The dry material of claim 1, wherein the weight of the particles of polymer C is approximately 0.1 to 20 times the weight of the dry matrix.

18. A process for the preparation of the dry material of claim 1, comprising the steps of:
(1) mixing, in amounts effective to form, after the cooling (2) and drying (3) steps recited below, said dry material,
(a) an aqueous solution of a macromolecular substance A capable of forming, after cooling to a temperature of 30° to 80° C., a porous aqueous gel when the substance A is in the presence of water, at a concentration of said substance A effective for forming the gel at a temperature of 30° to 80° C.,
(b) a water-soluble linear polymer B,
(c) a plasticizer for the macromolecular substance A, and
(d) a latex of a polymer C obtained from at least one water-immiscible monomer, wherein said polymer C has a glass transition temperature greater than 30° C. and can also contain reactive functional groups and wherein said mixing occurs at a temperature greater than the gelling temperature of the aqueous solution of the macromolecular substance A:
(2) cooling the resultant mixture to a temperature less than the gelling temperature of the aqueous solution of the molecular substance A and shaping, during the cooling, the aqueous gel obtained; and
(3) drying the shaped aqueous gel at a temperature less than the gelling temperature of said aqueous solution of the molecular substance A to obtain said dry material.

19. The process of claim 18, wherein the macromolecular substance A is agarose.

20. The process of claim 18, wherein the water-soluble linear polymer B is a linear polyacrylamide.

21. The process of claim 18, wherein the quantity of the water-soluble linear polymer employed is approximately 2 to 10 times the weight of the dry matrix.

22. The process of claim 18, wherein the plasticizer for the macromolecular substance A is a polyhydric alcohol.

23. The process of claim 18, wherein the quantity of plasticizer is 1 to 3 times the weight of the dry matrix.

24. The process of claim 18, wherein the polymer C forming the latex has a glass transition temperature greater than 60° C.

25. The process of claim 18, wherein the polymer C forming the latex is derived from at least one water-immiscible polymer selected from the group consisting of a vinylaromatic monomer, an alkyl ester of an α-β unsaturated acid, an ester of an unsaturated carboxylic acid, vinylchloride, vinylidene chloride, a conjugated diene, an unsaturated monomer containing at least one nitrile group, and a siloxane.

26. The process of claim 18, wherein the polymer C forming the latex is obtained from (1) a water-immiscible monomer and (2) less than 10% by weight, relative to the total weight of the water-immiscible monomer(s), of at least one comonomer which carries an ionogenic or reactive group.

27. The process of claim 26, wherein said comonomer is selected from the group consisting of vinylbenzene sulfonate, a sulfoalkyl ester of an unsaturated acid, an unsaturated carboxylic acid, a hydroxyalkyl acrylate or methacrylate, an aminoalkyl ester of an unsaturated acid, acrylamide, vinylbenzyl chloride and glycidyl methacrylate.

28. The process of claim 18, wherein the latex of polymer C is a latex of an alkali-soluble or acid-soluble polymer.

29. The process of claim 18, wherein the particles of polymer C forming the latex can be magnetized.

30. The process of claim 18, wherein the particles of polymer C forming the latex have a particle size of the order of 0.05 to 20 μm.

31. The process of claim 18, wherein the latex of polymer C contains from 5 to 30% by weight of particles of polymer C.

32. The process of claim 18, wherein the weight of the particles of polymer C corresponds to approximately 0.1 to 20 times the weight of the dry matrix.

* * * * *